United States Patent
Yamaguchi et al.

(10) Patent No.: US 7,355,691 B2
(45) Date of Patent: Apr. 8, 2008

(54) DEFECT INSPECTION APPARATUS AND DEFECT INSPECTION METHOD

(75) Inventors: Noboru Yamaguchi, Kikuchi-gun (JP); Yuudai Ishikawa, Kumamoto (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 11/540,681

(22) Filed: Oct. 2, 2006

(65) Prior Publication Data

US 2007/0076195 A1 Apr. 5, 2007

(30) Foreign Application Priority Data

Sep. 30, 2005 (JP) .............................. 2005-288563

(51) Int. Cl.
*G01N 21/00* (2006.01)
(52) U.S. Cl. .................................. 356/237.4
(58) Field of Classification Search ..................... None
See application file for complete search history.

(56) References Cited

U.S. PATENT DOCUMENTS 5,838,433 A * 11/1998 Hagiwara .................... 356/364

2004/0081917 A1* 4/2004 Tanaka et al. ............... 430/311

FOREIGN PATENT DOCUMENTS

JP 9-329555 A 12/1997

* cited by examiner

*Primary Examiner*—Tu T Nguyen
(74) *Attorney, Agent, or Firm*—Sughrue Mion, PLLC

(57) ABSTRACT

An irregularity defect inspection apparatus for inspecting an object to be inspected having a repeated pattern composed of regularly arranged unit patterns on the surface thereon to detect an irregularity defect occurring in the repeated pattern. The apparatus includes a light source apparatus having a light source for applying light to a region including an inspection region of the object to be inspected at a desired incidence angle, and an observation apparatus having a light-receiving optical system for receiving light which is generated from the inspection surface of the object to be inspected perpendicularly thereto when light is applied by the light source apparatus. The light source apparatus is provide with a light source having a parallelism of 2 degrees or less and an illuminance of 300000 Lx or higher.

16 Claims, 8 Drawing Sheets

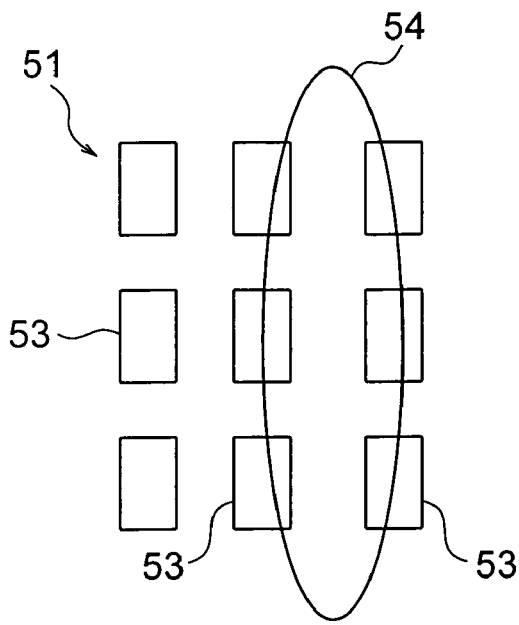
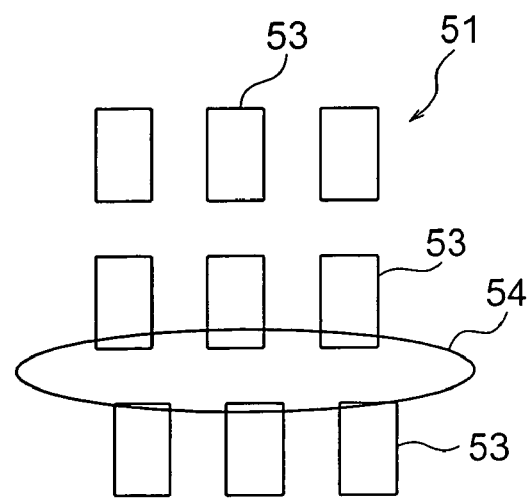
FIG. 4A          FIG. 4B
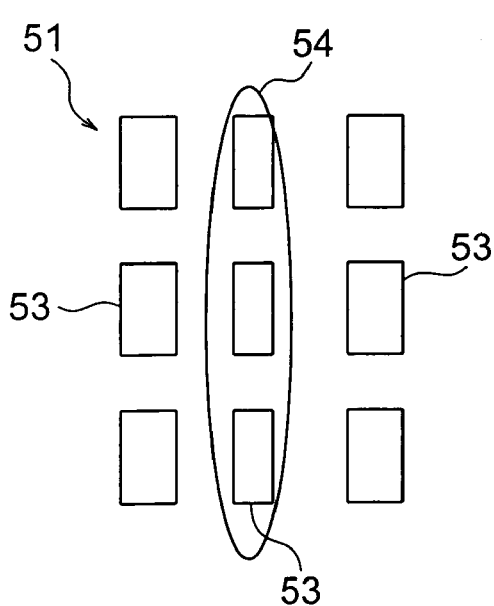
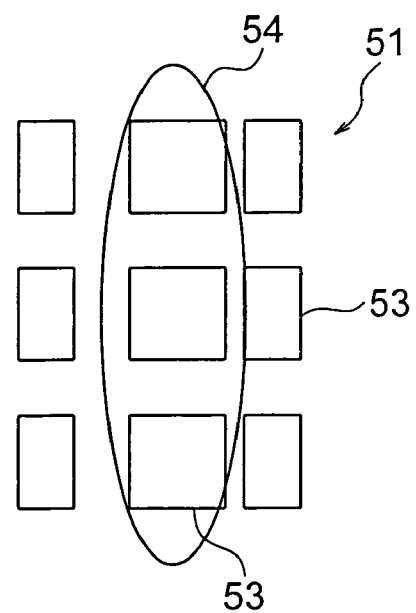
FIG. 4C          FIG. 4D

DEFECT INSPECTION APPARATUS AND DEFECT INSPECTION METHOD

This application claims priority to prior Japanese patent application JP 2005-288563, the disclosures of which are incorporated herein by reference.

BACKGROUND OF THE INVENTION

The present invention relates to a defect inspection apparatus and a defect inspection method for inspecting defects in a repeated pattern in an image device or a memory device, or for inspecting defects in a repeated pattern on a photomask used to form the pattern on an image device or a memory device. The present invention also relates to a method of manufacturing a photomask using such a defect inspection apparatus and a defect inspection method. The present invention further relates to a pattern transferring method using such a photomask and to a semiconductor wafer manufacturing method using such a photomask or a defect inspection method.

Conventionally, a defect inspection has been conducted as one of inspection items to inspect patterns formed on the surfaces of an image device such as an imaging device or a display device, or of a photomask used for manufacturing the image device. For example, there may occur an error in which patterns having different regularity are unintentionally included in patterns which otherwise should be arranged in uniform regularity. Such error is sometimes referred to as an irregularity defect. This kind of defects is caused by some or other reasons in the manufacturing process.

The presence of an irregularity defect in an imaging device or a display device may induce irregularity in sensitivity or display, which may lead to deterioration of device performance. Also, if an irregularity defect is present in a pattern of a photomask used for manufacturing an image device such as an imaging device or a display device, the irregularity defect will be transferred to the pattern of the image device, which may lead to deterioration of performance of the image device.

According to conventional techniques, such irregularity defect in patterns on image devices or photomasks often cannot be detected by shape inspection of individual patterns for the reason that micro defects are usually arranged regularly. However, when the defective region is viewed as a whole, it looks different from other normal regions. Therefore, the irregularity defect inspection is principally conducted visually by an operator using an oblique viewing inspection method or the like.

However, such visual inspection involves a problem that inspection results vary depending on the operator. Therefore, there is a demand for an automated irregularity defect inspection apparatus capable of performing an irregularity defect inspection automatically.

A macro inspection apparatus for semiconductor wafers is one of such apparatuses designed to automate the oblique viewing inspection. For example, Japanese Unexamined Patent Application Publication (JP-A) No. H09-329555 (hereafter referred to as Patent Document 1) discloses a macro inspection apparatus which includes a light source for applying light with a desired wavelength to a periodic structure on a semiconductor wafer, a camera for receiving diffracted light from the substrate surface, and detection means for detecting a defect by comparing image data taken by the camera with reference image data involving no defect. This macro inspection apparatus is designed to inspect the entire surface of a wafer with a single field of view to detect focus offset, defocus caused by the wafer position being vertically shifted due to presence of dust (particles) under the wafer, and surface defects in the semiconductor wafer structure arising in the development, etching, and release processes of the wafer. When inspecting a semiconductor wafer that is an object to be inspected having a periodic structure (a repeated pattern 151 having unit patterns 153 arranged regularly) as shown in FIG. 5 by the defect inspection using diffracted light as disclosed in Patent Document 1, the diffraction formula $$d(\sin \theta m \pm \sin \theta i) = m\lambda \quad (1)$$

can be used when a pitch of the periodic structure is denoted by d, the incidence angle is denoted by $\theta i$, the diffraction angle when the order of diffracted light is m is denoted by $\theta m$, and the wavelength of incident light is denoted by $\lambda$. However, since zeroth order diffracted light (direct light) contains no micro defect information, the order of diffracted light should be of an absolute value greater than zero in order to obtain micro defect information. As seen from the formula (1) above, the diffraction order and the diffraction angle vary depending on the pitch of the periodic structure.

According to the description of Patent Document 1, the direction of diffracted light and the wavelength of incident light are changed to obtain first-order diffracted light according to the range of pitches of 0.6 μm to 4 μm given in the design rule currently applied to semiconductor wafers. As a specific method for changing the diffraction angle, Patent Document 1 also discloses provision of a camera installed at several different angles.

However, when a wafer surface is viewed from an oblique direction by changing the angle of a camera serving as an observation apparatus as described in Patent Document 1, the distance between the camera object lens and the object is not uniform. This induces a problem that the resulting image of the surface has perspective, whereby the image of a repeated pattern which is originally supposed to have uniform dimensions are made ununiform or the focus is deviated in the surface. As a result, it is required to correct the perspective by image processing or the like, and such processing is complicated. In order to enable correct observation of irregularity without using such complicated processing, it is most desirable to arrange the light-receiving optical system of the observation apparatus directly above an object to be inspected so that the light-receiving optical system can receive light that is generated perpendicularly from the surface of the object to be inspected when irradiated with light from the light source apparatus.

However, as shown in FIG. 6, when an observation apparatus 113 is arranged directly above an object to be inspected 150, and incident light (incident light Ri when detecting reflected light, or incident light Ri' when detecting transmitted light) is applied to the object to be inspected 150 from a light source (a light source 112 when detecting reflected light, or a light source 112' when detecting transmitted light), the object lens (not shown) of the observation apparatus 113 will capture not only n-order diffracted light Rm (the absolute value of n is greater than zero) but also zeroth order diffracted light R0 including no defect information that is reflected or transmitted at an zeroth order diffraction angle $\theta 0$ that is the same angle as an incidence angle $\theta i$, if the incidence angle $\theta i$ is small, depending on an irradiated region (an irradiated region A when detecting reflected light, or an irradiated region A' when detecting transmitted light) that is defined by the spot diameter of the light source 112 or 112', a distance B between the object to be inspected 150 and the object lens of the observation apparatus 113 that is determined by focus control when a camera is used to capture an image of the object to be inspected, and the diameter D of the object lens of the observation apparatus 113. As a result, a large amount of light including no defect information is contained in the light captured by the observation apparatus 113, resulting in deterioration of contrast in defect information.

In contrast, if a light source apparatus is arranged at a position where the light from the light source apparatus is incident at a relatively large incidence angle, the observation apparatus will capture diffracted light having an order the absolute value of which is even higher as seen from the formula (1). Although the diffracted light having an order the absolute value of which is high is advantageous in capturing fine structures, the light quantity is reduced as the absolute value of the order becomes higher, as shown in FIG. 7. In this case, the sensitivity of the camera tends to be insufficient, inducing a problem of difficulty to observe defects.

Moreover, the inspection must support a very wide range of pixel pitches. For example, when the inspection is conducted on a display device such as a liquid-crystal panel or large-sized photomask used for manufacture of such device, the inspection must support pixel pitches ranging from 50 to 800 µm. When the object to be inspected is a semiconductor wafer for use in an imaging device such as CCD, the pixel pitch ranges from 0.5 to 8 µm, and when the object to be inspected is a photomask used in manufacture of a semiconductor wafer for an imaging device such as CCD, the pixel pitch ranges from 8 to 50 µm. As the pitch d of a repeated pattern becomes greater, the absolute value of the order of the diffracted light becomes higher. Therefore, even if the incidence angle is set to a minimum possible value at which no zeroth order diffracted light is captured, the absolute value of the order of the diffracted light becomes so high that the quantity of light becomes insufficient to detect irregularity. Further, the light quantity of the diffracted light is varied not only depending on the pitch d of the repeated pattern but also depending on an edge-to-edge width a of the repeated pattern (see FIG. 5). Therefore, it is possible that the light quantity becomes insufficient depending the edge-to-edge width a of the object to be inspected.

The insufficient light quantity may be complemented by a method of highlighting a defect by performing image processing such as highlight processing on an image captured by a camera having insufficient sensitivity. In this case, however, irregularities attributable to the camera itself are also captured, which is not desirable.

SUMMARY OF THE INVENTION

The present invention has been made for solving the problems as mentioned in the above, and an object of the present invention is to provide a pattern defect inspection apparatus and a defect inspection method which are able to observe a uniform observation region without performing complicated image processing and are able to sufficiently detect a defect in repeated patterns having various pitches of a wide variety of objects to be inspected. According to the present invention, a light-receiving optical system is arranged directly above the object to be inspected so as to receive light which is generated perpendicularly from the inspection surface of the object to be inspected when light is applied from the light source apparatus.

In order to achieve the object above, the present invention has aspects as follows.

(First Aspect)

A first aspect of the present invention relates to a defect inspection apparatus for inspecting an object to be inspected having a repeated pattern comprising regularly arranged unit patterns on the surface thereof to detect a defect occurring in the repeated pattern, and the defect inspection apparatus includes: a light source apparatus having a light source for applying light to a region including an inspection region of the object to be inspected at a desired incidence angle; and an observation apparatus having a light-receiving optical system for receiving light which is generated from the inspection surface of the object to be inspected perpendicularly thereto when light is applied by the light source apparatus. The light source applies the light having a parallelism of 2 degrees or less and an illuminance of 300000 Lx or higher.

(Second Aspect)

A second aspect of the present invention relates to the defect inspection apparatus according to the first aspect, wherein the light source comprises an extra-high pressure mercury lamp.

(Third Aspect)

A third aspect of the present invention relates to the defect inspection apparatus according to the first aspect, wherein the light source apparatus is arranged at a position to make such an incident angle that the light-receiving optical system receives substantially no zeroth order diffracted light.

(Fourth Aspect)

A fourth aspect of the present invention relates to the defect inspection apparatus according to the first aspect, wherein the observation apparatus has an imaging device for capturing an image with the use of the light received by the light-receiving optical system.

(Fifth Aspect)

A fifth aspect of the present invention relates to the defect inspection apparatus according to the first aspect, wherein the object to be inspected is an image device, a memory device, or a photomask used for manufacture thereof.

(Sixth Aspect)

A sixth aspect of the present invention relates to a defect inspection method for inspecting an object to be inspected having a repeated pattern comprising regularly arranged unit patterns on the surface thereof to detect a defect occurring in the repeated pattern, and the method includes the steps of applying light to a region including an inspection region of the object to be inspected at a desired incidence angle, and receiving light generated from the inspection surface of the object to be inspected perpendicularly thereto. In the method, the light is emitted from a light source having a parallelism of 2 degrees or less and an illuminance of 300000 Lx or higher.

(Seventh Aspect)

A seventh aspect of the present invention relates to the defect inspection method according to the sixth aspect, wherein the light receiving step is performed by a light-receiving optical system receiving diffracted light of a higher order than zero generated by the object to be inspected.

(Eighth Aspect)

An eighth aspect of the present invention relates to the defect inspection method according to the sixth aspect, wherein the light receiving step is performed by a light-receiving optical system receiving diffracted light of seventh or higher order generated by the object to be inspected.

(Ninth Aspect)

A ninth aspect of the present invention relates to the defect inspection method according to the sixth aspect, wherein the light source comprises an extra-high pressure mercury lamp.

(Tenth Aspect)

A tenth aspect of the present invention relates to the defect inspection method according to the sixth aspect, wherein the incidence angle is such that the light-receiving optical system receives substantially no zeroth order diffracted light.

(Eleventh Aspect)

An eleventh aspect of the present invention relates to the defect inspection method according to the sixth aspect, wherein an image is captured with the use of light received by the light-receiving optical system, and the inspection is performed based on the captured image.

(Twelfth Aspect)

A twelfth aspect of the present invention relates to the defect inspection method according to the sixth aspect, wherein the object to be inspected is an image device, a memory device, or a photomask used for manufacture thereof.

(Thirteenth Aspect)

A thirteenth aspect of the present invention relates to a photomask manufacturing method including the steps of: forming a light shielding film on a transparent substrate; forming a resist film on the light shielding film; irradiating the resist film with light to plot a predetermined pattern thereon, the predetermined pattern including a repeated pattern comprising regularly arranged unit patterns; selectively removing the plotted portion or non-plotted portion of the resist film to form a resist pattern; etching the light shielding film with the resist pattern used as a mask to form a pattern on the light shielding film; and removing the residual resist. The method further includes a defect inspection step in which light is applied at a desired incidence angle to an inspection surface of the resist pattern or the light shielding film having the pattern formed thereon, and diffracted light of a higher order than zero generated perpendicularly to the inspection surface is received by a light-receiving optical system. According to this method, the light is emitted by a light source having a parallelism of 2 degrees or less and an illuminance of 300000 Lx or higher.

(Fourteenth Aspect)

A fourteenth aspect of the present invention relates to a pattern transferring method comprising the steps of preparing a photomask having a pattern, and using the photomask to transfer the pattern. In the pattern transferring method, the photomask is manufactured by a method comprising the steps of: forming a light shielding film on a transparent substrate; forming a resist film on the light shielding film; irradiating the resist film with light to plot a predetermined pattern thereon, the predetermined pattern including a repeated pattern comprising regularly arranged unit patterns; selectively removing the plotted portion or non-plotted portion of the resist film to form a resist pattern; etching the light shielding film with the resist pattern used as a mask to form a pattern on the light shielding film; and removing the residual resist. The photomask manufacturing method further comprises a defect inspection step in which light is applied at a desired incidence angle to an inspection surface of the resist pattern or the pattern formed in the light shielding film, and diffracted light of a higher order than zero generated perpendicularly to the inspection surface is received by a light-receiving optical system. The light emitted by a light source has a parallelism of 2 degrees or less and an illuminance of 300000 Lx or higher.

(Fifteenth Aspect)

A fifteenth aspect of the present invention relates to a method of manufacturing a semiconductor wafer comprising the steps of preparing a photomask having a pattern, and using said photomask to transfer the pattern. In the method, the photomask is manufactured by a method comprising the steps of: forming a light shielding film on a transparent substrate; forming a resist film on the light shielding film; irradiating the resist film with light to plot a predetermined pattern thereon, the predetermined pattern including a repeated pattern comprising regularly arranged unit patterns; selectively removing the plotted portion or non-plotted portion of the resist film to form a resist pattern; etching the light shielding film with the resist pattern used as a mask to form a pattern on the light shielding film; and removing the residual resist. The photomask manufacturing method further comprises a defect inspection step in which light is applied at a desired incidence angle to an inspection surface of the resist pattern or the pattern formed in the light shielding film, and diffracted light of a higher order than zero generated perpendicularly to the inspection surface is received by a light-receiving optical system. The light emitted by a light source has a parallelism of 2 degrees or less and an illuminance of 300000 Lx or higher.

(Sixteenth Aspect)

A sixteenth aspect of the present invention relates to a semiconductor wafer manufacturing method according to the fifteenth aspect, the method including an defect inspection step for inspecting a semiconductor wafer having a repeated pattern comprising regularly arranged unit patterns on the surface thereof to detect a defect occurring in the repeated pattern, wherein the defect inspection step is performed by applying light at a desired incidence angle to an inspection surface, and receiving diffracted light of a higher order than zero generated perpendicularly to the inspection surface with a light-receiving optical system. According to the method, the light is emitted by a light source having a parallelism of 2 degrees or less and an illuminance of 300000 Lx or higher.

According to the fist or sixth aspect of the invention, the use of a light source having desirable parallelism as the light source makes it possible to expose an irregularity defect more notably. Additionally, the use of a light source having a high brightness (high illuminance) increases the quantity of light received by the light-receiving optical system, which extends the range of observable diffracted light and makes it possible to observe diffracted light of an order the absolute value of which is high. As a result, an irregularity defect inspection can be conducted on a wide variety of objects to be inspected having repeated patterns with various pitches even if the incidence angle is limited due to restrictions imposed on the apparatus by arranging the light-receiving optical system at a position directly above the object to be inspected where the most uniform image can be received. Therefore, a uniform observation region can be observed without involving complicated image processing, and a defect can be detected sufficiently from repeated patterns with various pitches on a wide variety of objects to be inspected.

According to the second or ninth aspect, the use of an extra-high pressure mercury lamp as the light source makes it possible to obtain light with desirable parallelism and high brightness (high illuminance) as described above.

According to the third or tenth aspect, the reception of light including no irregularity defect information is prevented and the detection of an irregularity defect is facilitated, by arranging the light source apparatus at a position to make such an incidence angle that the light-receiving optical system does not receive zeroth order diffracted light, namely at a position where the light-receiving optical system substantially receives only diffracted light of an order the absolute value of which is greater than zero.

According to the fourth or eleventh aspect, the analysis using image data is enabled by providing the observation apparatus with an imaging device for capturing an image with the use of light received by the light-receiving optical system.

According to fifth or twelfth aspect, the object to be inspected is an image device or a photomask which has a repeated pattern. Therefore, the defect inspection apparatus of the present invention is particularly suitable for inspecting such object to be inspected for an irregularity occurring therein.

BRIEF DESCRIPTION OF THE DRAWINGS

FIGS. 4A to 4D show irregularity defects which occurred in a repeated pattern formed on a chip of a photomask used in Example 1, FIGS. 4A and 4B showing coordinate-variation-type irregularity defects, while FIG. 4C and 4D showing dimensional-variation-type irregularity defects;

DESCRIPTION OF THE PREFERRED EMBODIMENTS

Preferred embodiments of the present invention will be described with reference to the accompanying drawings.

First Embodiment

Figure 1:
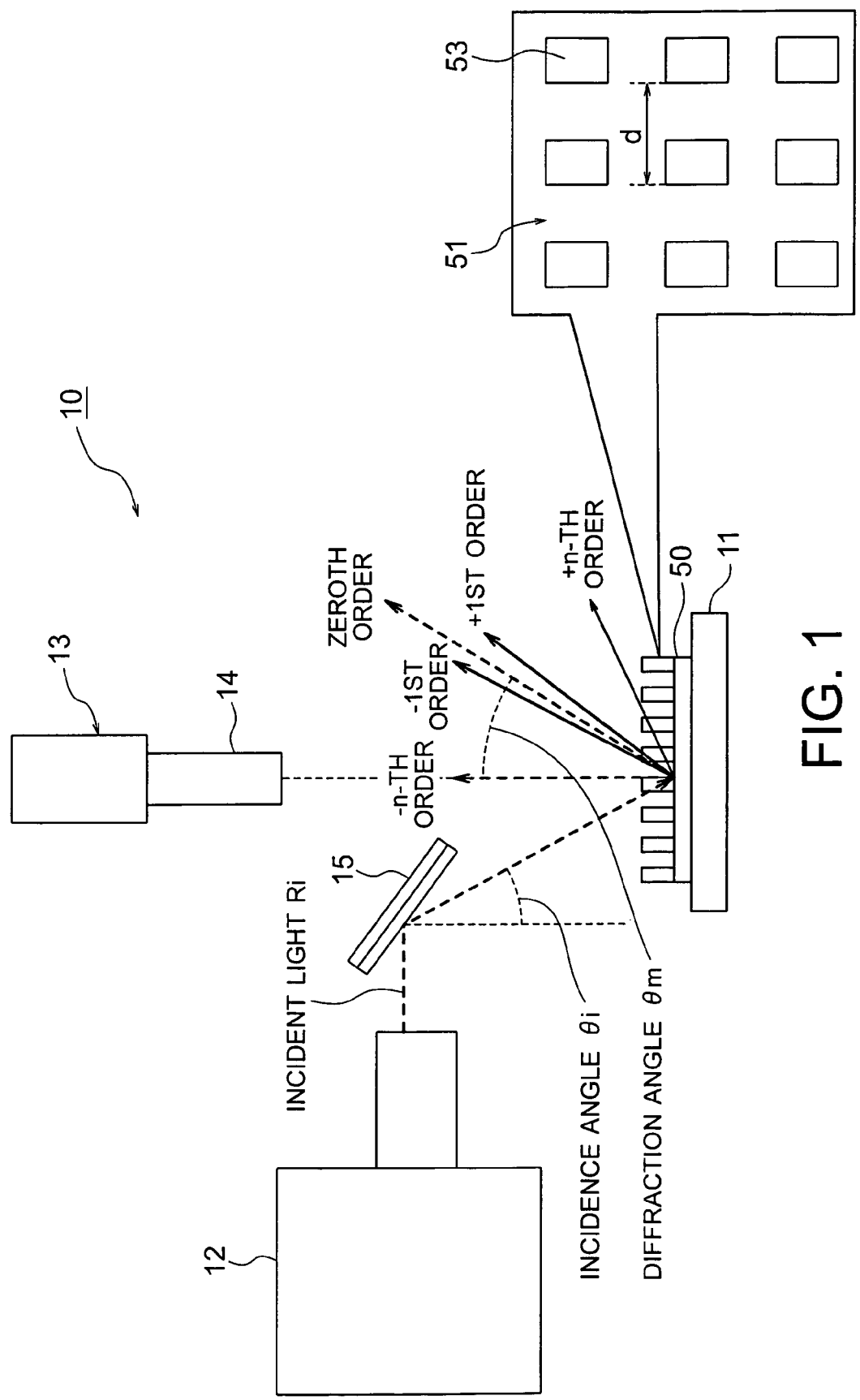
FIG. 1 is a schematic diagram illustrating a pattern defect inspection apparatus according to a first embodiment of the present invention.
Figure 2:
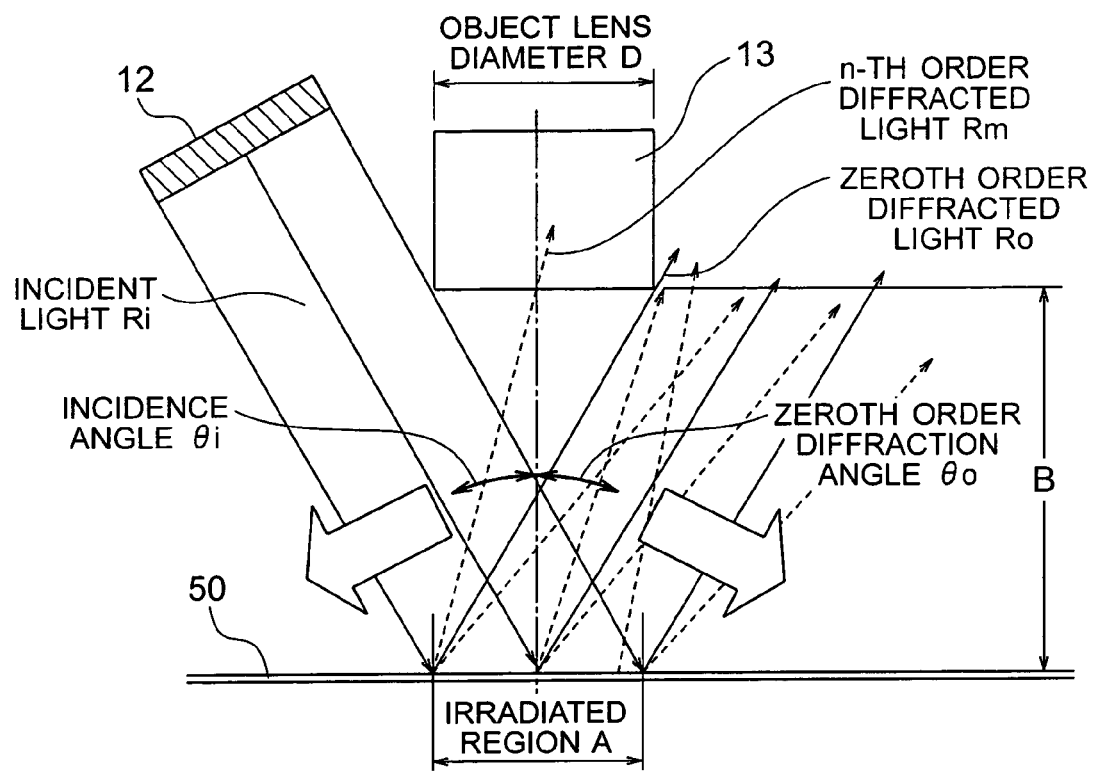
FIG. 2 is a diagram for explaining incidence angles of incident light in relation to the defect inspection apparatus of FIG. 1.

FIG. 1 is a perspective view showing schematic configuration of a pattern defect inspection apparatus according a first embodiment of the present invention. This embodiment relates to an example of an irregularity defect inspection apparatus which uses reflected light to inspect patterns for irregularity.

The irregularity defect inspection apparatus 10 shown in FIG. 1 includes a stage 11, a light source apparatus 12, an observation apparatus 13, and a light-receiving optical system 14 provided in the observation apparatus 13.

The stage 11 of the irregularity defect inspection apparatus 10 shown in FIG. 1 is a table to place an object to be inspected 50.

The stage 11 can be provided by an X-Y stage which is movable in X and Y directions so that an inspection region on the object to be inspected 50 can be designated. The stage 11 is rotatable around an axis vertical to the inspection surface of the object to be inspected 50 so as to enable inspection of the inspection surface using from various directions thereto.

The light source apparatus 12 uses a light source having high brightness (having an illuminance of 300000 Lx or higher) and high parallelism (having a parallelism of 2 degrees or less). An extra-high pressure mercury lamp is most desirable as a light source satisfying these conditions. The extra-high pressure mercury lamp has a smaller light emitting body in comparison with a xenon lamp or metal halide lamp with the same power, and yet has higher brightness and higher light-emitting efficiency. Therefore, the extra-high pressure mercury lamp is able to provide an ideal point light source, which makes it easy to obtain parallel rays. The light-emitting efficiency of the extra-high pressure mercury lamp is higher than of the xenon lamp, and thus accurate light with high energy can be obtained. Additionally, in comparison with lamps having a long light emitting body (having a long electrode interval) such as a low-pressure mercury lamp or a high-pressure mercury lamp, the extra-high pressure mercury lamp, which has an arc size that is very close to that of a point light source, is able to provide light having uniformity and high parallelism that is easy to converge or diffuse in an optical system. Therefore, uniform illuminance distribution can be obtained by using an extra-high pressure mercury lamp. When an extra-high pressure mercury lamp with high power (W) is used, a high illuminance is obtained but the parallelism is deteriorated. Therefore, the power of the extra-high pressure mercury lamp should be selected in consideration of the balance between parallelism and illuminance. The term parallelism as used herein means an angle over which light is diffused with respect to the light going straight. Light with a low parallelism can be obtained by collimating light emitted from the light source by means of a lens or a slit. More preferably, the parallelism should be one degree or less.

In this embodiment, the illuminance is 300000 Lx or higher, and more preferably 400000 Lx or higher. It is practical to set the illuminance to 800000 Lx or lower. The illuminance values mentioned above are based on the measurement results obtained by using an Ushio USR-40V/D spectroradiometer (illuminance meter).

It is preferable to use a light source having small illuminance distribution for the purpose of obtaining light of uniform intensity all over the inspection surface. Specifically, the illuminance distribution (that is defined by measuring illuminances, with a 5-μm pinhole mask mounted on the light receiving surface of the spectroradiometer, at five points consisting of the center and upper, lower, left and right points, and representing the ratio between the maximum and minimum illuminances by percentage) is preferably ±10% or less, and more preferably ±7% of less. The illuminance distribution also tends to be reduced when a lamp with high power (W) is used. Therefore, the light source should be selected in consideration of the balance between illuminance distribution and illuminance. An extra-high pressure mercury lamp excels also in the fact that small illuminance distribution can be obtained at high illuminance.

It is preferable to use a light source having a wavelength in the range of 380 to 800 nm. If the light from the light source contains ultraviolet light having a wavelength less than 380 nm, a security problem will occur when a visual inspection is performed. If the light from the light source contains infrared light having a wavelength greater than 800 nm, the light generates heat, which may exert adverse effects on the object to be inspected and the observation apparatus. From the same point of view, it is more preferable to use a light source having a wavelength from 400 to 750 nm. An extra-high pressure mercury lamp has a bright-line spectrum having wavelength peaks of a relative intensity of 50% or more at 405 nm, 436 nm, 546 nm, and at 579 nm. Therefore, an inspection can be performed using light containing monochromatic components in the wavelength range of 380 nm to 800 nm. This improves the contrast of an irregularity defect in comparison with light having a broad bright-line spectrum. The selection of a wavelength range is preferably performed with a wavelength filter provided in the light source apparatus.

Further, a wavelength filter may be provided between the light source and the object to be inspected or between the object to be inspected and the observation apparatus, when more precise selection of a light wavelength or wavelength band is desired for such a reason that a certain type of irregularity defect is exposed more depending on the used wavelength or wavelength band.

The light source apparatus 12 is arranged above one side of the stage 11. A mirror 15 is used to deflect light from the light source apparatus 12 so that the light is applied from obliquely above to a repeated pattern 51 composed of unit patterns 53 regularly arranged on the surface of the object to be inspected 50. Although the incidence angle can be adjusted by using an optical fiber, the use of the optical fiber may cause loss of the light quantity. Therefore, it is preferable to adjust the incidence angle by using a mirror to deflect the incident light when the light source apparatus should not be inclined, for example in such a case of the one having an extra-high pressure mercury lamp.

The observation apparatus 13 is provided with for example a CCD camera having an object lens as an imaging device. The observation apparatus 13 is arranged directly above the object to be inspected 50 (directly above the position where the center of the object lens matches the center of the inspection region of the object to be inspected). The arrangement of the observation apparatus 13 directly above the object to be inspected 50 reduces the problems that will arise when the observation apparatus 13 is obliquely arranged, namely, the problems that the distance between the object lens and the object to be inspected is not uniform, and thus the image of the surface has perspective to make ununiform the images of the unit patterns in the repeated pattern which normally should have uniform dimensions or to deviate the focus in the surface.

The object lens of the observation apparatus 13 is preferably a zoom lens capable of adjusting the focus in a wide range in order to enable the observation apparatus 13 to support various sizes of objects to be inspected and various pitches in their periodic structure. For the same reason, the observation apparatus 13 is preferably movable in a vertical direction.

When the observation apparatus 13 is arranged directly above the object to be inspected 50 as described above, the incidence angle should be set to a certain angle or greater so that the observation apparatus 13 receives diffracted light of an order the absolute value of which is greater than zero of zeroth order diffracted light (direct light).

The use of a camera such as a CCD camera as the observation apparatus 13 makes it possible to capture an image by means of the CCD camera and to display the captured image on a display screen. Further, the image can be analyzed as data by an analyzing apparatus (not shown). An ocular lens may be used as the observation apparatus 13.

The inspection methods using an analyzing apparatus include a method of setting a threshold value for acquired image data itself, and a method of setting a threshold value for a differential signal with respect to defect-free data. The latter inspection method, so-called compare check, has an advantage that noises other than those relating to defects can be eliminated, but has a disadvantage that it is difficult to obtain completely defect-free data when actual data is used as the defect-free data since comparison with pattern data is not possible in case of irregularity inspection. In comparison therewith, the former inspection method, which uses acquired image data itself, is similar to visual inspection, and enables simple and accurate inspection as long as the irregularity defect can be made distinguishable from the noise components.

The object to be inspected 50 may be an image device such as an imaging device and a display device, a memory device, and a photomask used for manufacture of such devices. The imaging device is represented by a solid-state imaging device such as CCD, CMOS, or VMIS. The display device is represented by a liquid-crystal display, a plasma display, an EL display, an LED display, or a DMD display. The memory device is represented by a semiconductor memory such as DRAM or SRAM. The object to be inspected 50 may include various types of substrate, such as a semiconductor wafer, a color filter, or an active matrix substrate for use in the devices as mentioned in the above.

When inspecting a photomask, the inspection may be conducted either from the top surface (patterned surface) or from the rear face of the photomask. This means that the inspection surface of the object to be inspected 50 is a surface on which a diffracted image of a repeated pattern can be obtained.

When the object to be inspected 50 is a display device such as a liquid-crystal panel or a large-sized photomask that is used in manufacture thereof, the pixel pitch thereof is 50 to 800 µm. The pixel pitch of a semiconductor wafer for an imaging device such as CCD is 0.5 to 8 µm, and the pixel pitch of a photomask used in manufacture of a semiconductor wafer for an imaging device such as CCD is 8 to 50 µm. The irregularity inspection apparatus according to this embodiment of the invention is able to cope with all these pitches.

When the repeated pattern has a small pitch, the absolute value of the order of diffracted light also becomes small. This may induce a condition in which the light quantity from the light source is too high, and the inspection is made difficult under the too bright light. In this case, the light quantity may be reduced by using an optical filter for example.

A description will be made of a method of detecting irregularity defects by using the irregularity defect inspection apparatus according to this embodiment of the present invention.

An object to be inspected 50 is placed on the stage 11 and an inspection region is designated on the object to be inspected 50.

Light is applied to the object to be inspected 50 from the light source apparatus 12 that is set at a predetermined incidence angle. Subsequently, focus control is performed by the observation apparatus 13 arranged directly above the inspection region to capture an image of the inspection region. The inspection region need not necessarily be the entire region on the surface that is irradiated with light from the light source, and may be a part of the irradiated region. The inspection is performed to detect irregularity defects based on the image thus captured.

Second Embodiment

Figure 3:
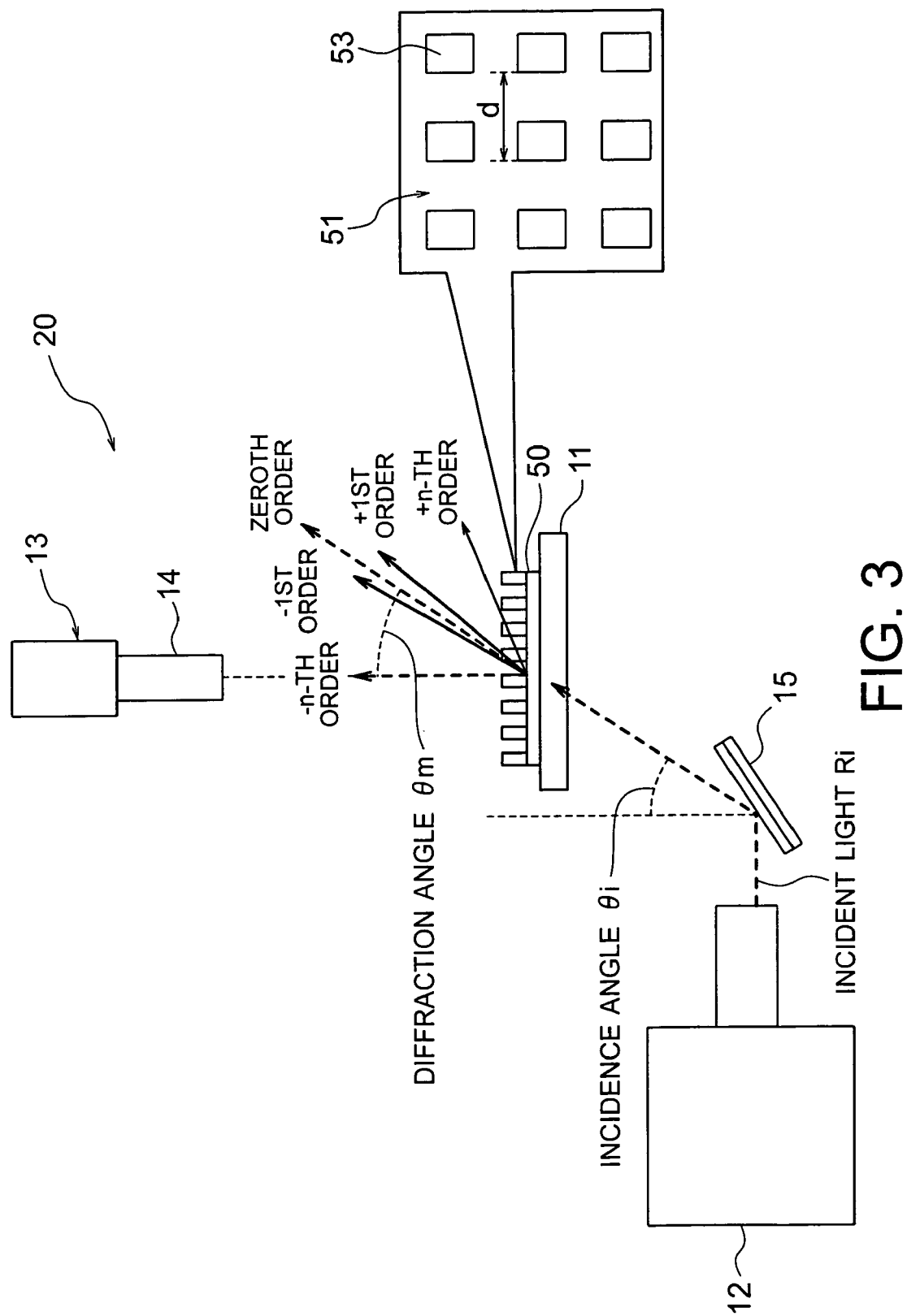
FIG. 3 is a schematic diagram illustrating a pattern defect inspection apparatus according to a second embodiment of the present invention.
Figure 5:
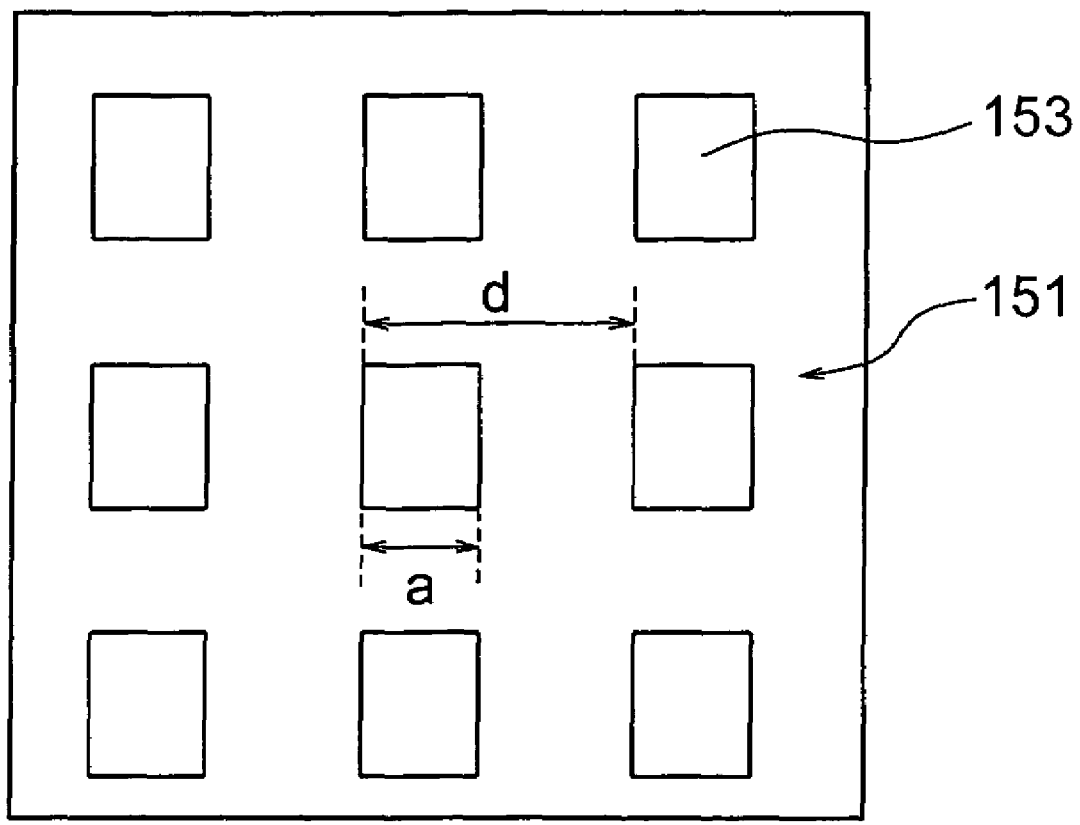
FIG. 5 is a schematic diagram showing a periodic structure of an object to be inspected.
Figure 6:
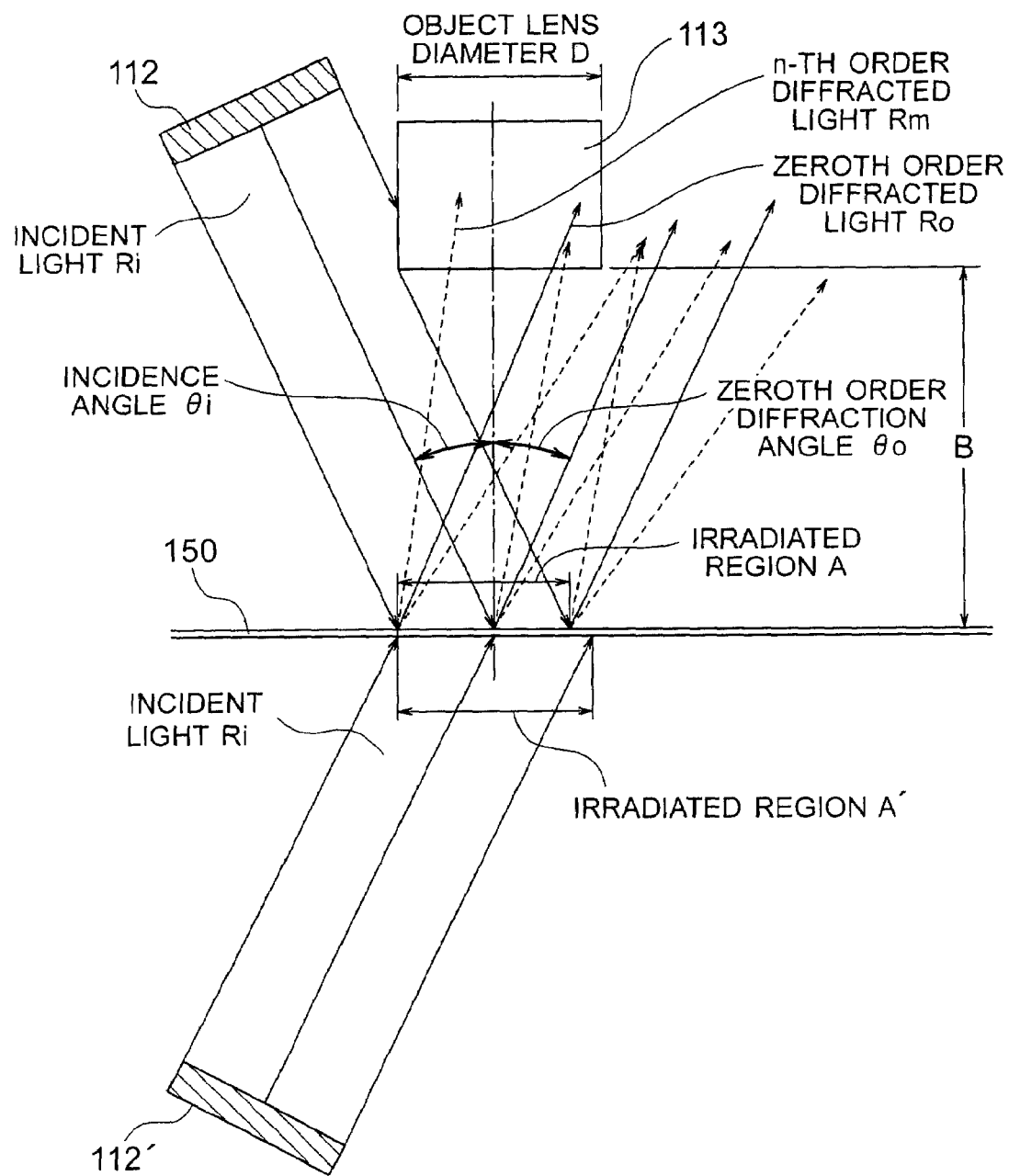
FIG. 6 is a diagram for explaining a problem that a conventional irregularity defect inspection apparatus has.
Figure 7:
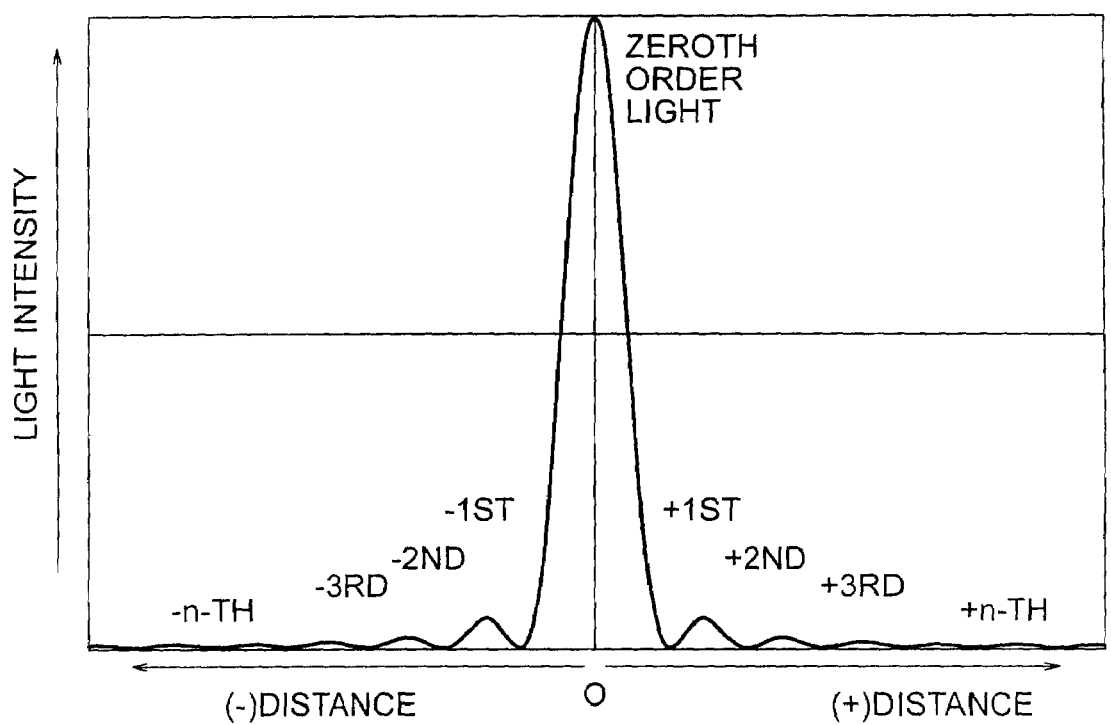
FIG. 7 is a graph showing light intensity relative to an order of diffracted light.

FIG. 3 is a perspective view schematically showing a pattern defect inspection apparatus according to a second embodiment of the present invention. This second embodiment relates to an example of irregularity defect inspection apparatus for detecting pattern irregularity by using transmitted light.

The irregularity defect inspection apparatus 10 shown in FIG. 3 includes a stage 11, a light source apparatus 12, an observation apparatus 13, and a light-receiving optical system 14 provided in the observation apparatus 13.

This second embodiment of the present invention is the same as the first embodiment except that the light source apparatus 12 is arranged below the object to be inspected 50, so that light from the light source apparatus 12 is applied to the object to be inspected 50 from below to inspect the same by using light transmitted through the object to be inspected.

The object to be inspected 50 to which this embodiment of the present invention is suitably applicable is an object which transmits light through between unit patterns in the repeated pattern. The second embodiment is particularly advantageous in inspection of a repeated pattern formed on a transparent substrate, for example, of a photomask used in manufacture of an image device such as an imaging device and a display device.

Figure 8A:
FIG. 8A is a drawing showing results of inspection in which a test pattern having irregularity defects is inspected by the defect inspection method according to the present invention.
Figure 8B:
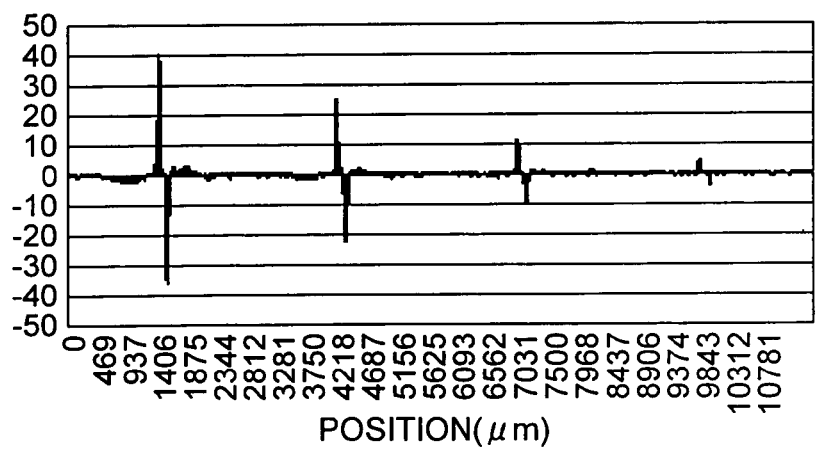
FIG. 8B is a chart showing the results obtained by differentiating the densities in the inspection results of FIG. 8A.

FIG. 8A shows a result of inspection conducted by the method of the present invention on a test pattern having an irregularity defect. The test pattern, having dimensional irregularities (to be described later) of 10 to 100 nm in 12 μm pitch repeated pattern (main patterns), was observed and image-captured by the apparatus according to the present invention. The inspection result apparently exhibits heterogeneous diffracted light (disturbance diffracted light) in the light diffracted by the main pattern, which is attributable to the irregularity defect. Four vertical lines in FIG. 8A indicate the detection results of the irregularity defect caused by dimensional deviations of 100 nm, 50 nm, 20 nm, and 10 nm, respectively, from the left to the right. FIG. 8B is a chart showing the results obtained by differentiating the densities in the inspection results of FIG. 8A.

The present invention will be described in further detail below, using working examples.

Example 1

An inspection was conducted on a photomask for use in formation of a CCD light-receiving element and having 8 μm pitch repeated dot patterns, with the use of the inspection apparatus according to the first embodiment.

The observation apparatus 13 was provided by a ½-inch CCD camera with an object lens of a zoom type of 0.39 to 4.7 magnification, having a numerical aperture (NA) of 0.10, and a lens diameter of 50 mm. Using this CCD camera, the area of the inspection region that can be imaged by one shot was a square of side about 1.5 to 20 mm. The object lens was brought into focus on the object to be inspected by moving the camera in a vertical direction and adjusting the focus of the camera, whereby the distance between the object lens and the object to be inspected was set to about 100 mm.

The light source was provided by an extra-high pressure mercury lamp of 500 W power, having an illuminance of 400000 Lx, an illuminance distribution of ±5%, and a parallelism of 0.6 degrees. When the incidence angle was set to 30 degrees, the region of 50 mm diameter was irradiated with light. In this case, if the extra-high pressure mercury lamp has a wavelength range of 405 to 580 nm, the diffracted light reflected perpendicular to the object to be inspected is of seventh to tenth order based on the formula (1) above.

A description will now be made of the photomask for forming a CCD receiving element, that is the object to be inspected in Example 1. A photomask is typically fabricated by providing a light shielding film of chromium or the like on a transparent substrate of synthetic quartz glass or the like, and removing a part of the light shielding film to form a desired pattern. The photomask inspected in this Example was formed of 5×5 chips each having a repeated pattern in which unit patterns were arranged regularly.

In general, this type of photomask is manufactured by first forming a light shielding film on a transparent substrate, and forming a resist film on this light shielding film. Subsequently, an electron beam or a laser beam is applied from a plotter to the resist film to expose the same in a predetermined pattern. A resist pattern is then formed by selectively removing the plotted portion or the non-plotted portion. The light shielding film is then etched while being masked with the resist pattern to form a repeated pattern on the light shielding film. Finally, the residual resist is removed to complete the manufacture of a photomask.

In the manufacture process as described above, when the resist film is directly plotted by the electron or laser beam scanning, joints may be produced in the plotted pattern depending on a beam diameter or a scanning width, and an error may occur periodically in these joints due to defective plotting. This contributes to occurrence of the irregularity defect.

FIGS. 4A to 4D show examples of such irregularity defects. In these figures, irregularity defect regions are denoted by the reference numeral 54. FIG. 4A shows an irregularity defect in which the spaces between the unit patterns 53 in a part the repeated pattern 51 are different from the normal space due to occurrence of positional deviation in the joints of patterns plotted by the beam. FIG. 4B also shows an irregularity defect in which the positions of some unit patterns 53 are deviated with respect to other normal unit patterns 53 in the repeated pattern 51 due to occurrence of positional deviation in the joints of patterns plotted by the beam. These irregularity defects shown in FIGS. 4A and 4B are referred to as the coordinate-variation-type irregularity defect. On the other hand, FIGS. 4C and 4D show irregularity defects in which the width of some of the unit patterns 53 in the repeated pattern 51 becomes smaller or greater than the normal width due to variation in intensity of the beam emitted by the plotter. These irregularity defects are referred as the dimensional-variation-type irregularity defect.

Irregularity defect inspections were conducted with the use of the irregularity defect inspection apparatus in Example 1, whereby there could be detected an irregularity defect caused by the positional deviation as shown in FIG. 4B and exhibiting an amount of positional deviation of 10 nm, as well as a dimensional-variation-type irregularity defect as shown in FIGS. 4C and 4D and exhibiting an amount of dimensional variation of 10 nm.

Example 2

An inspection was conducted on an 8-inch size semiconductor wafer composed of a plurality of chips of a size of 4 mm square each having a 2 μm pitch repeated pattern, with the use of the same inspection apparatus as in Example 1. In this case, if the extra-high pressure mercury lamp has a wavelength range of 405 to 580 nm, the diffracted light reflected perpendicular to the object to be inspected is of second order based on the formula (1) above.

It is believed that the semiconductor wafer may have photomask-induced irregularity which exhibits the same tendency as that of the irregularity of the photomask used to transfer the patterns, and another type of irregularity induced by the semiconductor wafer manufacturing process such as irregularity in application of resist.

In Example 2, chips to be inspected were selected from the chips on the semiconductor wafer and inspection was conducted on each inspection region selected from the chips to be inspected.

The inspections resulted in observation of irregularities exhibiting transverse stripes which were assumed to be photomask-induced irregularities, and irregularities exhibiting oblique stripes which were assumed to be induced by the process of manufacturing the semiconductor wafer.

Thus, in Example 2, the irregularities could be evaluated for each chip on the semiconductor wafer.

The embodiments and working examples described above provide advantageous effects as described in (1) to (4) below.

(1) Irregularity defects can be made apparent by using a light source having a desirable parallelism as the light source of the light source apparatus 12. Moreover, the use of the light source having a high brightness (high illuminance) increases the quantity of light received by the light-receiving optical system 14, whereby the range of observable diffracted light is extended to diffracted light of an order of a high absolute value. As a result, it is made possible to detect irregularity defects from an object to be inspected 50 having a repeated pattern with a wide range of pitches, even if the incidence angle θi is limited due to the restrictions imposed on the apparatus by fixedly arranging the light-receiving optical system directly above the object to be inspected to allow the same to receive the most uniform image. Accordingly, the most uniform observation region can be observed without performing complicated image processing. Moreover, defects can be detected sufficiently even from a wide variety of repeated patterns 51 with various pitches on various types of object to be inspected 50 such as an image device, a memory device, or a photomask used for manufacture thereof.

(2) The use of an extra-high pressure mercury lamp as the light source of the light source apparatus 12 makes it possible to obtain light having desirable parallelism and high brightness (high illuminance).

(3) The light source apparatus 12 is arranged at a position where the incidence angle θi is such that the light-receiving optical system 14 does not receive zeroth order diffracted light, that is, where the light-receiving optical system 14 receives only the diffracted light of an order the absolute value of which is greater than zero. This makes it possible to prevent the reception of light including no irregularity defect information, and facilitates the detection of irregularity defects.

(4) The observation apparatus 13 is provided with a CCD camera which captures an image with the use of light received by the light-receiving optical system 14, whereby the analysis using image data is made possible.

What is claimed is:

1. A defect inspection apparatus for inspecting an object having a repeated pattern comprising unit patterns arranged with a regularity on the surface thereof to detect a defect having another regularity occurred in the repeated pattern, comprising:
   a light source apparatus having a light source for applying light to a region including an inspection region of the object an incidence angle; and
   an observation apparatus having a light-receiving optical system for receiving light which is generated from the inspection surface of the object perpendicularly thereto when light is applied by the light source apparatus, wherein the light source applies the light having a parallelism of 2 degrees or less, and an illuminance of 300000 Lx or higher,
   and said incidence angle is such that the light-receiving optical system being capable of receiving 7th or greater absolute value of order of diffracted light generated from the object.

2. The defect inspection apparatus according to claim 1, wherein the light source comprises an extra-high pressure mercury lamp.

3. The defect inspection apparatus according to claim 1, wherein the light source apparatus is arranged at a position to make the incident angle such that the light-receiving optical system receives 7th or greater absolute value of order of diffracted light generated from the object.

4. The defect inspection apparatus according to claim 1, wherein the observation apparatus has an imaging device for capturing an image with use of the light received by the light-receiving optical system.

5. The defect inspection apparatus according to claim 1, wherein the object is an image device, a memory device, or a photomask used for manufacture thereof.

6. A defect inspection method for inspecting an object having a repeated pattern comprising unit patterns arranged with a regularity on the surface thereof to detect a defect having another regularity occurred in the repeated pattern, the method comprising the steps of:
   applying light to a region including an inspection region of the object at an incidence angle; and
   receiving light generated from the inspection surface of the object perpendicularly thereto,
   wherein the light is emitted from a light source having a parallelism of 2 degrees or less and an illuminance of 300000 Lx or higher,
   and said incidence angle is such that the light-receiving optical system being capable of receiving 7th or greater absolute value of order of diffracted light generated from the object.

7. The defect inspection method according to claim 6, wherein the light source comprises an extra-high pressure mercury lamp.

8. The defect inspection method according to claim 6, wherein an image is captured with use of light received by the light-receiving optical system, and the inspection is performed based on the captured image.

9. The defect inspection method according to claim 6, wherein the object to be inspected is an image device, a memory device, or a photomask used for manufacture thereof.

10. A method of manufacturing a photomask comprising the steps of:
    forming a light shielding film on a transparent substrate;

forming a resist film on the light shielding film;
irradiating the resist film with light to plot a predetermined pattern thereon, the predetermined pattern including a repeated pattern comprising unit patterns arranged with a regularity;
selectively removing the plotted portion or non-plotted portion of the resist film to form a resist pattern;
etching the light shielding film with the resist pattern used as a mask to form a pattern on the light shielding film; and
removing the residual resist
wherein the method further comprises a defect inspection step for detecting a defect having another regularity, in which light is applied at an incidence angle to an inspection surface of the resist pattern or the pattern formed in the light shielding film,
and diffracted light of absolute value of seventh or greater order generated perpendicularly to the inspection surface is received by a light-receiving optical system, the light being emitted by a light source having a parallelism of 2 degrees or less and an illuminance of 300000 Lx or higher.

11. The method according to claim 10 wherein the photomask is for manufacturing liquid crystal panel, and said predetermined pattern includes a repeated pattern comprising unit patterns which is arranged with 50 to 800 micrometers pitches.

12. The method according to claim 10 wherein the photomask is for manufacturing CCD imaging device, and said predetermined pattern includes a repeated pattern comprising unit patterns which is arranged with 8 to 50 micrometers pitches.

13. The method according to claim 10, wherein the defect inspection step further comprises an image capturing with use of light received by the light-receiving optical system, and the inspection is performed with the captured image.

14. A pattern transferring method comprising the steps of:
preparing a photomask having a pattern; and using said photomask to transfer the pattern,
wherein said photomask is manufactured by a method comprising the steps of:
forming a light shielding film on a transparent substrate;
forming a resist film on the light shielding film;
irradiating the resist film with light to plot a predetermined pattern thereon, the predetermined pattern including a repeated pattern comprising unit patterns arranged with a regularity;
selectively removing the plotted portion or non-plotted portion of the resist film to form a resist pattern;
etching the light shielding film with the resist pattern used as a mask to form a pattern on the light shielding film; and
removing the residual resist,
wherein the photomask manufacturing method further comprises a defect inspection step for detecting a defect having another regularity in which light is applied at an incidence angle to an inspection surface of the resist pattern or the pattern formed in the light shielding film,
and diffracted light of absolute value of seventh or greater order generated perpendicularly to the inspection surface is received by a light-receiving optical system, the light being emitted by a light source having a parallelism of 2 degrees or less and an illuminance of 300000 Lx or higher.

15. A method of manufacturing a semiconductor wafer comprising the steps of: preparing a photomask having a pattern; and using said photomask to transfer the pattern,
wherein said photomask is manufactured by a method comprising the steps of:
forming a light shielding film on a transparent substrate;
forming a resist film on the light shielding film; irradiating the resist film with light to plot a predetermined pattern thereon, the predetermined pattern including a repeated pattern comprising regularly arranged unit patterns arranged with a regularity;
selectively removing the plotted portion or non-plotted portion of the resist film to form a resist pattern;
etching the light shielding film with the resist pattern used as a mask to form a pattern on the light shielding film; and
removing the residual resist,
wherein the photomask manufacturing method further comprises a defect inspection step for detecting a defect having another regularity in which light is applied at an incidence angle to an inspection surface of the resist pattern or the pattern formed in the light shielding film,
and diffracted light of absolute value of seventh or greater order generated perpendicularly to the inspection surface is received by a light-receiving optical system, the light being emitted by a light source having a parallelism of 2 degrees or less and an illuminance of 300000 Lx or higher.

16. A method of manufacturing a semiconductor wafer comprising an defect inspection step for inspecting a semiconductor wafer having a repeated pattern comprising unit patterns arranged with a regularity on the surface thereof to detect a defect having another regularity occurred in the repeated pattern,
wherein the defect inspection step is performed by applying light to an inspection surface at an incidence angle,
and receiving diffracted light of absolute value of seventh or greater order generated perpendicularly to the inspection surface with a light-receiving optical system, the light being emitted by a light source having a parallelism of 2 degrees or less and an illuminance of 300000 Lx or higher.

* * * * *